United States Patent [19]

Koehnke et al.

[11] Patent Number: 4,807,613
[45] Date of Patent: Feb. 28, 1989

[54] BANDAGE AND SHIELD

[76] Inventors: Raechelle K. Koehnke; Gregory H. Koehnke, both of 36 Gleason Dr., Iowa City, Iowa 52240

[21] Appl. No.: 945,912

[22] Filed: Dec. 22, 1986

[51] Int. Cl.4 ............... A61F 13/00; A61F 15/00
[52] U.S. Cl. ................... 128/155; 128/156; 206/440
[58] Field of Search .......... D24/49; 128/155, 156, 128/132 R; 206/440, 441; 604/389, 896, 897

[56] References Cited

U.S. PATENT DOCUMENTS

| D. 247,064 | 1/1978 | Spiegelberg | D9/193 |
|---|---|---|---|
| 2,133,609 | 10/1938 | Eustis | 128/155 |
| 2,897,961 | 8/1959 | Bush | 206/441 |
| 2,969,144 | 1/1961 | Zackheim | 206/441 |
| 3,085,024 | 4/1963 | Blackford | 206/441 X |
| 3,402,716 | 9/1968 | Baxter | 128/155 |
| 4,334,530 | 6/1982 | Hassell | 128/156 |
| 4,341,209 | 7/1982 | Schaar | 128/156 |
| 4,360,015 | 11/1982 | Mayer | 128/156 |
| 4,381,784 | 5/1983 | Aberson et al. | 604/368 |
| 4,390,519 | 6/1983 | Sawyer | 424/28 |
| 4,402,696 | 9/1983 | Gulko | 604/897 |
| 4,466,431 | 8/1984 | Tharrat et al. | 128/156 |
| 4,526,166 | 7/1985 | Silber | 128/156 |
| 4,570,627 | 2/1986 | MacConkey et al. | 128/155 |
| 4,664,106 | 5/1987 | Snedeker | 128/156 |

FOREIGN PATENT DOCUMENTS

| 0101298 | 2/1984 | European Pat. Off. | 128/156 |
|---|---|---|---|
| 1182766 | 1/1959 | France | 128/156 |

Primary Examiner—Richard J. Apley
Assistant Examiner—Paul Prebilik
Attorney, Agent, or Firm—Allan L. Harms

[57] ABSTRACT

Adhesive bandage with accompanying shield is disclosed. Bandage has non-adhesive extension depending from the bandage base. Shield has a flap which overlies non-adhesive extension of bandage. Shield is easily removed by persons with deficiencies in manual dexterity. Optional perforations between extension and base are disclosed.

6 Claims, 1 Drawing Sheet

BANDAGE AND SHIELD

BACKGROUND OF THE INVENTION

Bandages comprising adhesive sheets with absorbent material affixed thereto are well known. These devices are made in various shapes and sizes and usually include shield structures which will release from the adhesive of the bandage with some force which is usually less than that required to pull the adhesive sheet from the skin of the user. The shields are typically paired and overlap the non-adhesive absorbent material leaving ends which may be lifted and grasped in order to pull the shield from the bandage adhesive. Such shields are well known in the art. Such arrangements are very suitable for use by those with normal digital dexterity. However, many users of such bandages suffer disabilities with respect to manual or digital dexterity. Many geriatric patients experience difficulty with removal of the usual bandage shields because of reduced dexterity accompanying advanced age or because of such diseases or conditions as rheumatoid arthritis, and other debilitating diseases or conditions. When digital dexterity is lacking, the lifting of the bandage shield from its generally parallel position relative to the adhesive strip causes difficulty and also increases the risk of contamination of the absorbent material. The instant invention provides improvements to this bandage technology.

SUMMARY OF THE INVENTION

This invention relates to pressure-sensitive adhesive bandages with removable shields. A bandage having an absorbent pad affixed to a generally planar adhesive area is provided with an extension depending from the adhesive area which comprises a non-adhesive bearing portion. The non-adhesive extension is optionally connected to the adhesive backing by a perforated region to enable removal of the non-adhesive extension from the adhesive area if desired. In an elongated form of the invention, optionally, a second non-adhesive area may extend from the opposing end of the bandage. A shield is further provided which overlies the adhesive area, the absorbent pad and the non-adhesive extension of the bandage. In an alternative embodiment, the shield may include one or more folded or foldable portions at the end or ends thereof which are positioned to overlay the non-adhesive extension of the bandage.

An object of the invention is to provide a bandage and shield which provides improved removal of the shield therefrom.

Another object of the invention is to provide an improved bandage which may be removed by those with decreased manual dexterity.

Another object of the invention is to provide a bandage which allows facilitated removal of the shield therefrom with decreased risk of contamination of the absorbent pad of the bandage.

Those and other objects of the invention will be apparent from the detailed description and claims which follow.

DETAILED DESCRIPTION OF THE DRAWINGS

The present invention is directed to adhesive bandages of the well-known types and particularly to provide such bandages with improved means for removal from the bandage shield and user's skin.

Figure 3:
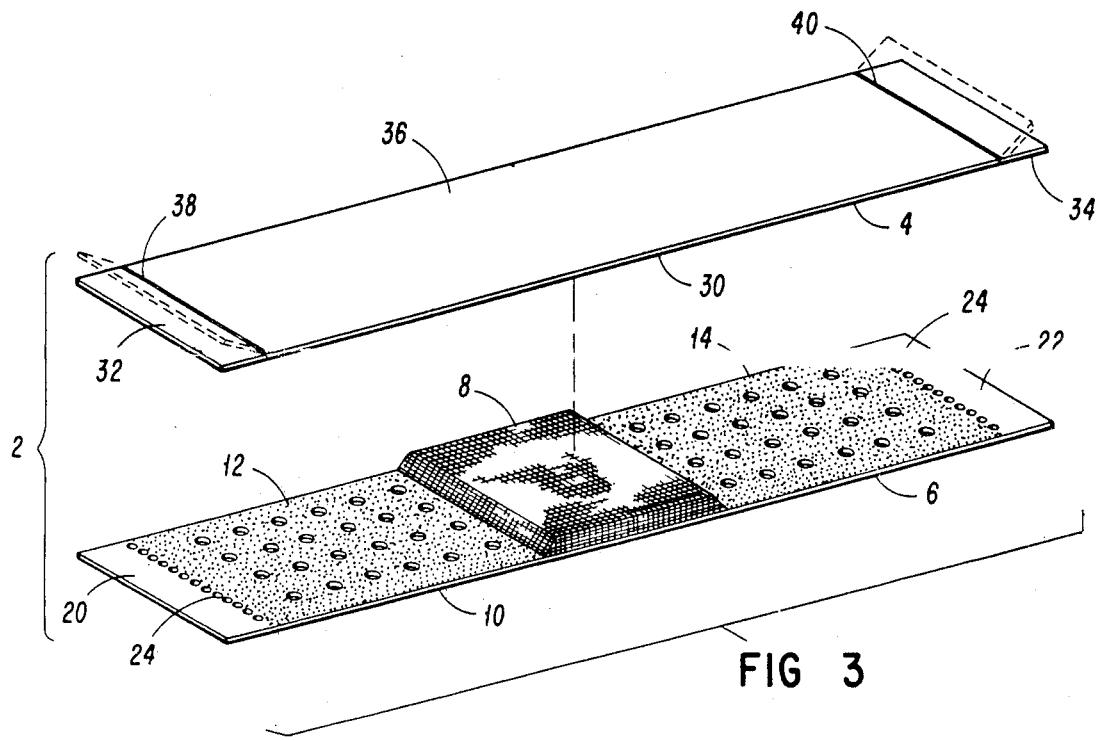
FIG. 3 is an exploded perspective view of the invention inverted from FIG. 1.

Referring to the drawing figures and in particular to FIG. 3, the invention 2 is shown with shield 4 separated from bandage 6. Pad 8, which is typically absorbent material, is fixed to base 10 of bandage 6 by adhesive or other suitable means. It is of course intended that pad 8 will be applied to the area on the user's skin to be treated and therefore pad 8 may be impregnated or coated with medications or other desired substances. In FIG. 3 is shown a pad 8 medially applied to an elongated base 10. However, other geometries of base 10 and pad 8 are equally contemplated.

Pressure-sensitive adhesive is applied to fastening elements 12 and 14 which, in the embodiment shown, are parts of base 10 of bandage 6 which extend from opposing sides of pad 8. Depending from fastening elements 12 and 14 are extensions 20 and 22 which, in the preferred embodiment, interconnected to fastening elements 12 and 14 respectively at perforations 24.

Figure 1:
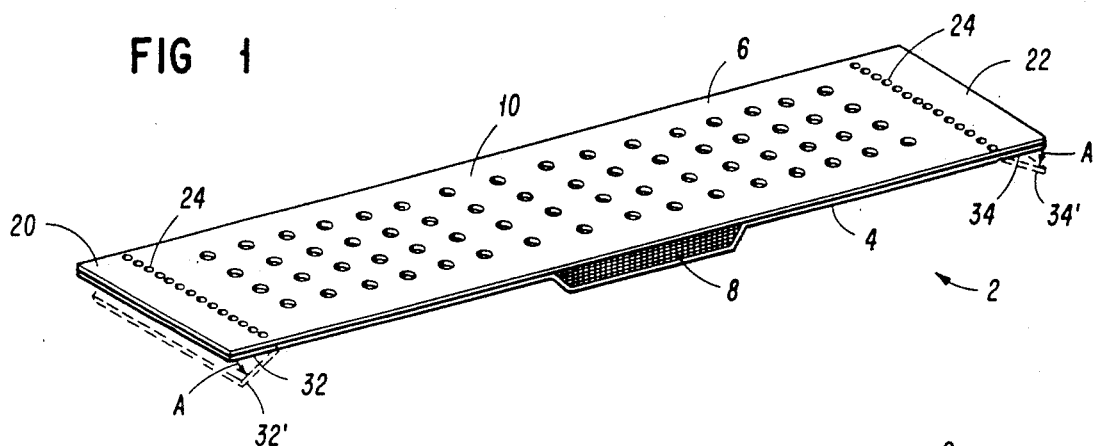
FIG. 1 is a perspective view of the invention.
Figure 2:
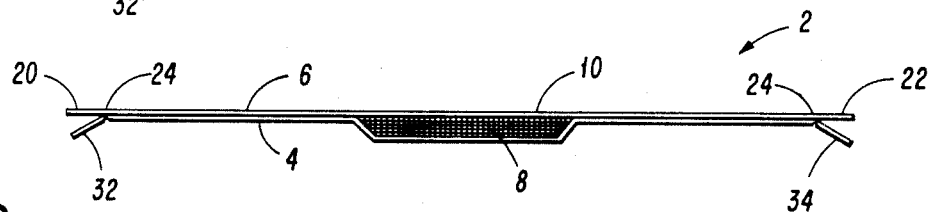
FIG. 2 is a front elevation of the invention.

Shield 4 comprises a sheet which is sized to generally overlie bandage 6. Surface 30 of shield 4, which faces the adhesive face of bandage 6, is provided with a highly calendared or other non-adhesive facing to allow easy removal of shield 4 from adhesive bearing fastening elements 12 and 14 without causing serious deterioration of the adhesive of fastening elements 12 and 14. Flaps 32 and 34 are disposed upon central body 36 of shield 4 at fold lines 38 and 40 respectively. Flaps 32 and 34 generally overlie extensions 20 and 22 of bandage 6. Because no adhesive joins flap 32 to extension 20 or flap 34 to extension 22, flaps 32 and 34 are free to pivot about fold lines 38 and 40 respectively in direction A as at 32' and 34' respectively as shown in FIG. 1. Similarly extensions 20 and 22 may be crimped or folded at perforations 24 to cause extensions 20 and 22 to be angularly displaced from the plane of base 10.

In the preferred embodiment, it is expected that flaps 32 and 34 will be prefolded at a small angle displaced from extensions 20 and 22 respectively. Alternatively, flaps 32 and 34 may exceed the size of extensions 20 and 22 such that the material of flaps 32 and 34 extend beyond extensions 20 and 22 to provide a free edge to grasp.

OPERATION OF THE INVENTION

Persons of limited dexterity, such as many geriatric patients or those suffering rheumatoid arthritis, in using invention 2 can easily remove shield 4 from bandage 6 by grasping flap 32 of shield 4 with one hand and extension 20 of bandage 6 with the other hand and pulling the shield 4 from the bandage 6. Similarly flap 34 and extension 22 may be grasped to pull apart shield 4 and bandage 6. Because of the non-adhesive surface of extension 20, and the easy deflection of flap 32 from linear about fold line 38, flap 32 is pivoted away from extension 20 and easily grasped. Persons with dexterity deficiencies have at least as much difficulty removing the bandage from the skin as in removing the shield from the bandage. After bandage 6 is applied to the skin of the user, extension 20 is available to assist in removal of bandage 6 from the user's skin when it is time to change the dressing.

Because extension 20 is separated from fastening element 12 by perforations 24, extension 20 may be removed by the user who does not wish to have extension 20 free to pivot about the skin surface.

Having described the invention, we claim:

1. In an adhesive bandage comprising a planar base having adhesive supplied to a face thereof, an absorbent pad affixed to said base intermediate the adhesive face thereof, and protective shield structure generally overlying said bandage, the improvement comprising a non-adhesive extension depending from said base, said shield structure comprising a releaseable sheet removably adhered to said adhesive face of said base, said sheet having a flap generally overlying said non-adhesive extension of said base, said flap being deflectable, said extension of said base is adjoined to said base by a perforated region.

2. The invention of claim 1 wherein said bandage and shield structure are generally elongated and said absorbent pad is medially disposed upon said base of said bandage, said non-adhesive extension depends from an end of said base, said releaseable sheet is generally similar in size and shape to said base.

3. The invention of claim 2 wherein said flap of said shield is determined by a fold line upon said sheet, said flap is foldable about said fold line.

4. The invention of claim 2 wherein said non-adhesive extension is a first non-adhesive extension, a second non-adhesive extension depends from said base generally opposite said first non-adhesive extension, said sheet having a second flap generally disposed upon said sheet to overlie said second non-adhesive extension, said second flap being deflectable, said second extension of said base is adjoined to said base by a perforated region.

5. The invention of claim 4 wherein said bandage and shield structure are generally elongated and said absorbent pad is medially disposed upon said base of said bandage, said non-adhesive extensions depend from opposing ends of said base, said releaseable sheet is generally similar in size and shape to said base.

6. In an adhesive bandage comprising a planar base having adhesive supplied to a face thereof, an absorbent pad affixed to said base intermediate the adhesive face thereof, and protective shield structure generally overlying said bandage, the improvement comprising a non-adhesive extension depending from said base, said shield structure comprising a releaseable sheet removably adhered to said adhesive face of said base, said sheet having a flap generally overlying said non-adhesive extension of said base, said flap being deflectable, said extension of said base is adjoined to said base by a weakened region.

* * * * *